United States Patent

(12) United States Patent
Van Herpen

(10) Patent No.: US 8,026,103 B2
(45) Date of Patent: Sep. 27, 2011

(54) BREATH TEST FOR TOTAL ORGANIC CARBON

(75) Inventor: Maarten Marinus Johannes Wilhelm Van Herpen, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 227 days.

(21) Appl. No.: 11/816,293

(22) PCT Filed: Feb. 16, 2006

(86) PCT No.: PCT/IB2006/050508
§ 371 (c)(1),
(2), (4) Date: Aug. 15, 2007

(87) PCT Pub. No.: WO2006/087683
PCT Pub. Date: Aug. 24, 2006

(65) Prior Publication Data
US 2009/0042309 A1    Feb. 12, 2009

(30) Foreign Application Priority Data
Feb. 18, 2005  (EP) .................................. 05300133

(51) Int. Cl.
*G01N 33/00*  (2006.01)
(52) U.S. Cl. ............. 436/143; 73/23.2; 73/23.3; 422/50; 422/84; 600/543
(58) Field of Classification Search .................. None
See application file for complete search history.

(56) References Cited

U.S. PATENT DOCUMENTS

| 3,607,071 A | 9/1971 | Staffin et al. |
| 4,047,894 A * | 9/1977 | Kuhl ............................ 261/101 |
| 4,272,486 A | 6/1981 | Harman, III |
| 4,294,583 A | 10/1981 | Leichnitz |
| 5,465,728 A | 11/1995 | Phillips |
| 6,292,756 B1 * | 9/2001 | Lievois et al. .................. 702/50 |
| 6,312,390 B1 | 11/2001 | Phillips |
| 6,794,645 B2 | 9/2004 | Kanik et al. |
| 2003/0109794 A1 | 6/2003 | Phillips |

FOREIGN PATENT DOCUMENTS

| DE | 2845319 | 5/1980 |
| WO | 02077636 | 10/2002 |

OTHER PUBLICATIONS

Tabatabai, M.A. et al., Use of the Leco Automatic 70-Second Carbon Analyzer for Total Carbon Analysis of Soils, 1970, Soil Science Society of American Journal, vol. 34(4), pp. 608-610.*
T.J. Vink et al: Personal Healthcare by Non-Invasive Breath Testing, Philips Research Technical Note PR-TN-2004/00389.

* cited by examiner

*Primary Examiner* — Yelena G Gakh
*Assistant Examiner* — Robert Xu

(57) ABSTRACT

A total amount of volatile organic compounds (VOCs) in a breath sample (101) is detected by oxidizing/burning (120) the VOCs to form $CO_2$ and $H_2O$, and the amounts of one or both of these compounds are measured (130). $CO_2$ and $H_2O$ molecules in the breath sample (101) are removed (110) before the VOCs are converted (120) to $CO_2$ and $H_2O$. Because one VOC molecule contains multiple carbon and hydrogen atoms, the number of formed $CO_2$ and $H_2O$ molecules will be substantially larger than the original number of VOC molecules, thereby improving the sensitivity of the detection.

20 Claims, 1 Drawing Sheet

BREATH TEST FOR TOTAL ORGANIC CARBON

This invention relates to the field of medical systems, and in particular to a breath analyzer that is particularly well suited for detecting total amounts of organic compounds.

U.S. Pat. No. 6,312,390 "BREATH TEST FOR DETECTION OF LUNG CANCER", issued 6 Nov. 2001 to Michael Phillips, and incorporated by reference herein, teaches the detection of elevated levels of volatile organic compounds (VOCs) in alveolar breath to identify the presence of lung cancer in mammals. VOCs in the alveolar breath is captured in a sorbent trap, using an apparatus as described in U.S. Pat. No. 5,465,728 "BREATH COLLECTION", issued 14 Nov. 1995 to Michael Phillips and incorporated by reference herein. The collected VOCs are thermally desorbed, then quantified and identified by mass spectroscopy. Twenty two VOCs, predominantly methylated alkanes, were shown to be present in statistically-significant higher amounts in patients with lung cancer.

U.S. Pat. No. 6,794,645 "PROTON-TRANSFER-REACTION/ION-MOBILITY-SPECTROMETER AND METHOD OF USING THE SAME", issued 21 Sep. 2004 to Kanik et al, and incorporated by reference herein, teaches that other illnesses, such as diabetes (higher acetones), periodontal disease (higher sulfur compounds), and liver cirrhosis (higher propanol) can be detected using breath analysis. A high-pressure ionizer uses $H_3O^+$ to ionize the large organic molecules, without ionizing the normal components of air ($O_2$, $N_2$, $CO_2$, CO, etc.), to isolate the organics. In this manner, the gas chromatography/mass spectrometry of the sample has less background noise.

Other VOCs are also indicative of the metabolic effects of other illnesses. Of particular note, oxidative stress has been implicated as a mechanism of aging and carcinogenesis, and is increased in several disorders, including rheumatoid arthritis, ischeamic heart disease, and bronchial asthma. Ethane and pentane have been identified as markers for oxidative stress. In like manner, aldehydes, including formaldehyde, acetaldehyde, and acetone, the secondary products of lipid peroxidation, are also indicative of oxidative stress.

In CLINICA CHIMICA ACTA 347 (Elsevier 2004), "Diagnostic Potential of Breath Analysis—Focus on Volatile Organic Compounds", at pages 25-39, Wolfram Miekisch et al. present a review of current diagnostic techniques based on VOCs.

U.S. Pat. No. 6,794,645 also notes the application of air sampling techniques beyond breath analysis, including the detection of illegal drugs such as cocaine, marijuana, and heroin, the detection of explosives, and environmental monitoring, as well as the detection of chemical markers of life on distant planets. Other uses of air samplers may include, for example, an air sampler in the cockpit of airplanes, or the cab of a train, to detect alcohol use, or in the air conduits of schools, factories, and office buildings to detect the presence of VOCs in the air that have been identified as carcinogens. Conventional techniques used for monitoring VOCs in an air sample typically include some form of spectrography to identify the individual VOC components.

U.S. Pat. No. 4,294,583 "HIGHLY SENSITIVE GAS MEASURING METHOD FOR THE ANALYSIS OF BREATH ALCOHOL CONCENTRATIONS, USING TEST TUBES", issued 13 Oct. 1981 to Leichnitz, and incorporated by reference herein, teaches the detection of alcohol by heating the breath in a pyrolysis oven to form carbon monoxide, and then detecting the level of carbon monoxide. Presumably, the pyrolysis oven is configured to limit the amount of oxygen being provided to the heated sample, to assure the production of carbon monoxide. To distinguish the amount of carbon monoxide produced from the alcohol from the amount of carbon monoxide in the breath of a smoker, the amount of carbon monoxide in the breath sample before the pyrolysis oven is also measured. A calorimetric carbon monoxide gas detector is used to measure the amounts of carbon monoxide in the samples.

It is an object of this invention to provide a relatively low cost method and system for detecting levels of VOCs in a patient's breath. It is a further object of this invention to provide a low cost breath analyzer that provides an indication of a patient's overall health. It is a further object of this invention to provide a relatively low cost air sampling method and system for VOCs.

These objects and others are achieved by a method and system that is configured to measure a total amount of oxidized compounds, such as $CO_2$ and $H_2O$, from which the amount of chemicals that were oxidized to form these compounds can be determined. Of particular note, the method and system can be used to measure a total amount of volatile organic compounds (VOCs) in a breath sample. The VOCs are oxidized/burned to form $CO_2$ and $H_2O$, and the amounts of one or both of these compounds are measured. Because one VOC molecule contains multiple carbon and hydrogen atoms, the number of formed $CO_2$ and $H_2O$ molecules will be substantially larger than the original number of molecules of VOCs, thereby improving the sensitivity of the detection. To assure that the measured $CO_2$ and $H_2O$ are the result of the oxidation of the chemicals of interest, the $CO_2$ and $H_2O$ molecules in the breath sample are removed from the sample before the chemicals of interest are converted to $CO_2$ and $H_2O$.

The invention is explained in further detail, and by way of example, with reference to the accompanying drawings wherein.

Throughout the drawings, the same reference numeral refers to the same element, or an element that performs substantially the same function. The drawings are included for illustrative purposes and are not intended to limit the scope of the invention.

This invention is premised on the observation that detecting the presence or absence of volatile organic compounds (VOCs) in a person's breath can provide meaningful information, without requiring an identification of the particular chemical within the class, and without determining the relative concentration of each particular chemical. Because the detection or non-detection of VOCs in a breath sample can be used as a general health indicator, a low-cost VOC breath analyzer can be expected to find a wide field of applications. For example, an embodiment of this invention could be used in a home environment, as a "first alert" screening tool, wherein if the detected amount of VOCs exceeds a given limit, the user is advised to go to a doctor for further tests. Alternatively, each doctor's office could be equipped with an embodiment of this invention, and the doctor uses it as one of many diagnostic tools for ruling-out or confirming alternative diagnoses, or as a preliminary screen before calling for expensive spectrometry tests. For example, if an abnormally high level of VOCs is not found using the tester at the doctor's office, there is no need to send the sample to a lab to determine the relative concentrations of the insignificant amounts of particular VOC compounds. These and other applications of a relatively low-cost VOC detector will be evident to one of ordinary skill in the art.

Figure 1:
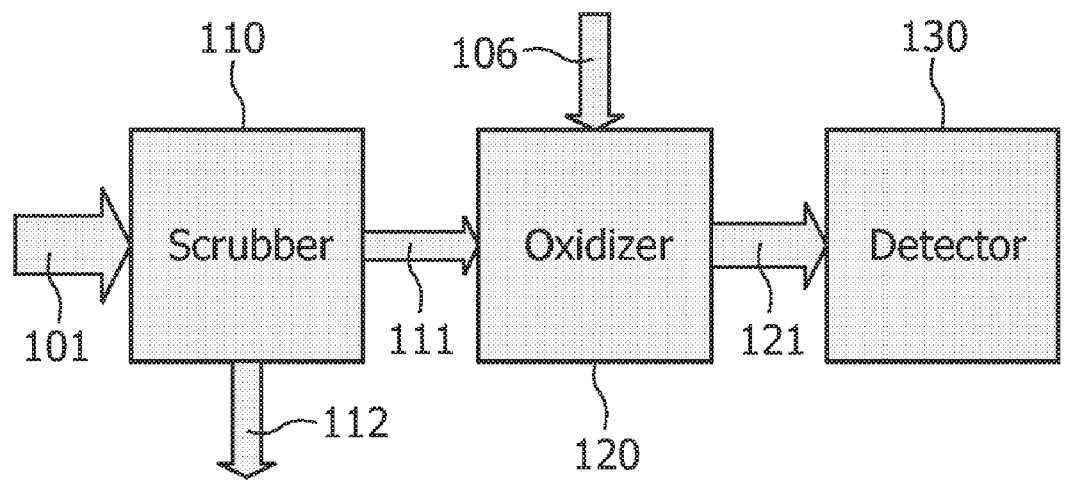
FIG. 1 illustrates an example block diagram of an air/breath analyzer in accordance with this invention.

FIG. 1 illustrates an example block diagram of an air/breath analyzer in accordance with this invention. Of particular note, the analyzer comprises an oxidizer 120, typically an oven, that converts molecules of an input gas 111 into an output gas 121 comprising, if the sample contains VOCs or other hydrocarbons, carbon dioxide ($CO_2$) and water ($H_2O$), as well as the other gases present in the input gas 111 that are not oxidized by the oxidizer 120. The detector 130 is configured to detect the amount of carbon dioxide, or water, or both, in the output gas 121. (For ease of reference, unless otherwise noted, the term "or" is used hereinafter in the inclusive sense, and includes "both".) As contrast with the pyrolysis oven used in U.S. Pat. No. 4,294,583, referenced above, the oxidizer 120 is configured to provide total, or near total, oxidation/burning of the input gas 111 to form carbon dioxide and water, and thus the amount of oxygen 106 being provided to the oxidizer 120 does not need to be controlled.

If the carbon dioxide or water in the output gas 121 is solely or predominantly produced by the hydrocarbons in the input gas 111, then the detected amount of carbon dioxide or water will be an indicator of the amount of hydrocarbons in the gas 111. Alternatively stated in a more general case, if a correlation can be determined or estimated between the amount of carbon dioxide or water in the output gas 121 and the amount of hydrocarbons in the input gas 111, then this correlation can be used to determine the amount of hydrocarbons in the input gas 111, based on the amount of the measured carbon dioxide and water in the output gas 121.

To assure that the total amount of the measured $CO_2$ or $H_2O$ is predominantly produced by the oxidation of the hydrocarbons in the gas 111, a "scrubber" 110 is configured to remove the naturally occurring $CO_2$ or $H_2O$ 112 from the breath sample 101 to form the input gas 111 that is to be oxidized.

The term scrubber is used in the general sense, and may include any device or method that removes select components from the input sample 101, either directly, indirectly, and/or via one or more stages. US Patent Application Publication 2003/0109794 "BREATH COLLECTION APPARATUS", by Michael Phillips, published 12 Jun. 2003, teaches the use of a condensation unit to remove water from an input sample. Using such a condenser as the scrubber 110, and a water detector as the detector 130, the input gas 111 to the oxidizer 120 will contain a minimal amount of water, and thus the amount of water determined by the detector 130 in the output gas 121 will be predominantly related to the amount of water produced by the oxidation of the hydrogen-based chemicals, such as VOCs, in the input gas 111, and correspondingly in the input sample 101. Other methods of removing water from the input sample 101 will be evident to one of ordinary skill in the art, including the use of a cooling trap that freezes the water in a sample, or the use of a chemical scrubber, such as calcium chloride (CaCl).

In like manner, for example, potassium hydroxide (KOH) can be used as the scrubber 110 to remove the $CO_2$ in the input sample 101, and the detector 130 can be configured to detect $CO_2$ in the output gas 121. In this manner, the amount of detected $CO_2$ in the gas 121 will be indicative of the amount of carbon-based chemicals, such as VOCs, in the input sample 101.

Note that the scrubber 110 can be configured to remove both $CO_2$ and $H_2O$ from the input sample 101, typically via a multi-stage scrubbing. In such an embodiment, the detector 130 can be configured to detect a combined amount of $CO_2$ and $H_2O$, for even greater precision and/or ease of measurement.

Any of a variety of techniques can be used to detect the amount of $CO_2$ and/or $H_2O$ in the scrubbed sample. In a preferred embodiment, spectroscopic techniques are used, and may include direct absorption spectroscopy, photoacoustic spectroscopy, cavity ring-down spectroscopy, frequency modulation spectroscopy, cavity enhanced absorption spectroscopy, and so on. For example, M. M. J. W. van Herpen et al. have disclosed an infrared laser system that is well suited for detecting $CO_2$ at levels below one part in a billion in "Real-time monitoring of the respiration of small insects and single cells with laser based $CO_2$ detection", Appl. Phys. Lett. (2003). Additionally, copending PCT application PCT/IB2006/050572, "PHOTOACOUSTIC SPECTROSCOPY DETECTOR AND SYSTEM", filed Feb. 22, 2006 for Hans van Kesteren of Koninklijke Philips Electronics N.V., and incorporated by reference herein, teaches a miniaturized photoacoustic detector that would be well suited for a compact embodiment of this invention.

The system thus described is particularly well suited for the detection of VOCs, because VOCs are relatively easy to oxidize/burn, and if a hydrocarbon is in a person's breath, it is likely to be a VOC. Further, each VOC molecule generally contains multiple carbon and hydrogen atoms, and thus the output gas 121 will generally have more molecules than the input gas 111, thereby easing the measurement task and/or increasing the precision of the detection process compared to a direct measure of the original VOC molecules. Additionally, because the invention is based on the detection of $CO_2$ and/or $H_2O$, the detector can be designed simply and efficiently, without regard to the particular VOCs that are being detected. Note that the system of this invention does not directly indicate which particular VOC is present in a person's breath, but if used as a general health indicator and/or a "first alert" indicator, the detection or non-detection of significant amounts of $CO_2$ or $H_2O$ produced by the oxidation of the breath sample can be informative. As is evident, there is some risk of false-alarms being caused by this non-selective testing, if, for example, a non-health-indicative hydrocarbon, such as alcohol, is present in the person's breath, but such false alarms should be rare if the system is used properly.

Figure 2:
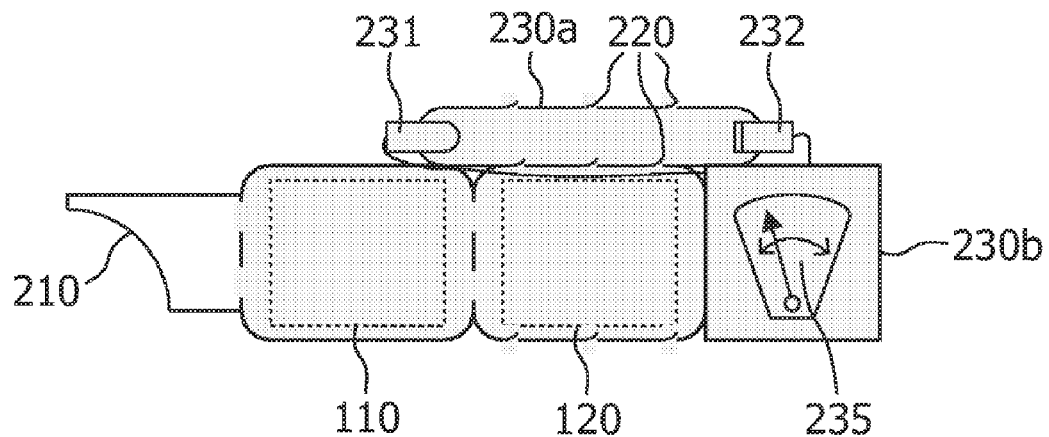
FIG. 2 illustrates an example breath analyzer in accordance with this invention.

FIG. 2 illustrates an example breath analyzer in accordance with this invention. A mouthpiece 210 provides a conduit for a breath sample to be collected in a scrubber 110. Consistent with conventional breath samplers, this mouthpiece 210 may be configured to bypass an initial sample of a user's breath, in order to assure that the collected sample is a sample of alveolar breath, after an initial discharge of non-alveolar, or 'surface' breath.

The scrubber 110 deletes carbon dioxide and/or water molecules from the sampled breath, using any of a variety of techniques, including chilling devices or chemical devices. The filtered breath from the scrubber 110 enters the oxidizer 120 that is configured to burn the gases from the scrubbed input sample.

At the transit between any of the components 210, 110, 120, 230a, valves 219 may be provided to assure that the desired sample is properly provided to the next stage in the process. One of ordinary skill in the art will recognize that ancillary air-movement apparatus may be used to facilitate the transfer between stages. For example, a syringe-type piston is commonly used in breath analyzers to draw the air through each stage, and the valves 219 are configured as one-way flap valves. In like manner, means may be provided to purge the components 110, 120, 230a of the breath sample, including, for example, a supply of relatively inert gas, such as nitrogen, to fill the components between samples. These and other techniques for obtaining a proper sample through the components 110, 120, 230*a* are common in the art.

In the example embodiment of FIG. 2, a photo-sensor is used for detecting the amount of carbon dioxide and/or water. A light source 231 provides light having a wavelength that allows the light to be absorbed by the molecules of either carbon dioxide or water. A dual light source may also be used to allow the light to be absorbed by both the carbon dioxide molecules and the water molecules. A light detector 232 is configured to measure the amount of light received, and thereby the amount of light absorbed by the detection molecules.

A monitor device 230*b* is configured to control the light source 231 and to receive the signals generated by the light detector 232. Preferably, the device 230*b* measures the amount of light received by the detector 232 before and after the sample is introduced into the detector 230*a*, so that the difference and/or ratio of the measures is used to determine the amount of absorption that has occurred. Alternatively, a separate detector (not illustrated) can be used to measure the intensity of the light emitted from the light source via a path that does not include the sampled gas, to get a concurrent measure of the difference and/or ratio of the measures.

The monitor device 230*b* includes a display element 235 that provides an indication of the amount of carbon dioxide and/or water that is detected. The element 235 is illustrated as a meter/gauge, although any means of informing the user of the results of the analysis may be used, including an audio signal, an LED display, a paper printout, and so on. In a preferred embodiment, as a "first alert" device, the monitor device 230*b* compares the measured amount of detected gases to one or more predefined thresholds, and merely presents an easy to comprehend indication, such as illuminating a red/green LED, or a red/yellow/green LED, and so on.

The foregoing merely illustrates the principles of the invention. It will thus be appreciated that those skilled in the art will be able to devise various arrangements which, although not explicitly described or shown herein, embody the principles of the invention and are thus within the spirit and scope of the following claims.

In interpreting these claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) each of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts is intended to be required unless specifically indicated; and i) the term "plurality of" an element includes two or more of the claimed element, and does not imply any particular range of number of elements; that is, a plurality of elements can be as few as two elements.

The invention claimed is:

1. An air analyzer for detecting volatile organic compounds, the air analyzer comprising:
    a scrubber configured to collect at least one alveolar breath sample and to substantially remove all molecules of naturally occurring carbon dioxide and water from the at least one alveolar breath sample to form a filtered sample;
    a converter configured to receive an uncontrolled amount of oxygen to convert molecules of hydrocarbons in the filtered sample to molecules of carbon dioxide and water to form an output sample; and
    a detector configured to detect an amount of water produced by oxidation of hydrogen-based chemicals in the filtered sample as an air analysis result,
    wherein the carbon dioxide and water in the output sample are produced by the hydrocarbons in the filtered sample and the detected amount of carbon dioxide and water indicate the amount of hydrocarbons in the at least one alveolar breath sample.

2. The air analyzer of claim 1, wherein the scrubber includes at least one of a condensing unit and a freezing unit.

3. The air analyzer of claim 1, wherein the scrubber includes at least one of potassium hydroxide (KOH) and calcium chloride (CaCl).

4. The air analyzer of claim 1, wherein the converter includes an oven that is configured to provide complete oxidation of the molecules of the hydrocarbons.

5. The air analyzer of claim 1, wherein the scrubber is configured to collect at least two air samples of alveolar breath of a mammal and further comprising a bypass configured to bypass an initial air sample of the at least two air samples.

6. The air analyzer of claim 1, further including one or more air exchange components that are configured to facilitate the transfer of air from the scrubber to the converter to the detector.

7. The air analyzer of claim 1, wherein the detector is configured to detect the water using optical spectroscopy.

8. The air analyzer of claim 1, wherein the detector includes a display element that is configured to indicate a presence of carbohydrates in the air sample.

9. The air analyzer of claim 8, wherein the display element includes a multicolor LED and the detector controls the multicolor LED based on a comparison of a measure of one or both of the carbon dioxide and water in the output sample to one or more predefined thresholds.

10. A method of detecting volatile organic compounds, the method comprising acts of:
    collecting at least one sample of gas;
    removing all molecules of naturally occurring carbon dioxide and water from the at least one sample of gas to form a reduced sample of gas that is substantially free of water;
    oxidizing the reduced sample of gas to transform volatile organic compounds in the reduced sample of gas into carbon dioxide and water to form an oxidized sample of gas; and
    detecting an amount of the carbon dioxide and water produced by oxidation of hydrogen-based chemicals in the reduced sample of gas,
    wherein the carbon dioxide and water in the output sample of gas are produced by the hydrocarbons in the reduced sample of gas and the detected amount of carbon dioxide and water corresponds to the volatile organic compound in the at least one sample of gas.

11. The method of claim 10, wherein the at least one sample of gas comprises an alveolar breath from a human, the method comprising acts of:
  collecting at least two samples of alveolar breath from a human; and
  bypassing an initial sample of the at least two samples of alveolar breath such that the volatile organic compounds of the initial sample of the alveolar breath are excluded from being detected.

12. The method of claim 10, wherein the act of removing the carbon dioxide and water includes cooling the at least one sample of gas to facilitate removal of the carbon dioxide and water in the at least one sample of gas.

13. The method of claim 10, wherein the act of removing the carbon dioxide and water includes an act of introducing at least one other chemical into the at least one sample of gas.

14. The method of claim 13, wherein the at least one other chemical includes at least one of calcium chloride (CaCl) and potassium hydroxide (KOH).

15. The method of claim 10, wherein the act of detecting the water in the oxidized sample includes acts of:
  transmitting light through the oxidized sample; and
  measuring an effect on the light as it propagates through the oxidized sample.

16. The method of claim 10, further including acts of:
  comparing a measure of the carbon dioxide and water in the oxidized sample of gas to a threshold amount; and
  providing an indication based on the comparison of the measure to the threshold amount.

17. The air analyzer of claim 1, wherein the scrubber is configured to substantially remove molecules of both of the carbon dioxide and water from the sample to form the filtered gas sample.

18. The air analyzer of claim 17, wherein the detector is configured to detect both of the carbon dioxide and the water in the output sample.

19. The method of claim 10, wherein the act of removing water from the at least one sample of gas comprises an act of removing both of carbon dioxide and water from the at least one sample of gas.

20. The method of claim 19, wherein the act of detecting the water in the oxidized sample of gas comprises an act of detecting both of the carbon dioxide and the water in the oxidized sample of gas.

* * * * *